United States Patent [19]

Osterburg et al.

[11] Patent Number: 4,760,204

[45] Date of Patent: Jul. 26, 1988

[54] PROCESS FOR DEODORIZING ISOPROPYL ALCOHOL

[75] Inventors: Günther Osterburg, Rheurdt; Karl-Heinz Gluzek, Alpen; Wolfgang Reith, Glinde; Wilhelm Neier, Rheinberg, all of Fed. Rep. of Germany

[73] Assignee: Deutsche Texaco Aktiengesellschaft, Hamburg, Fed. Rep. of Germany

[21] Appl. No.: 385

[22] Filed: Jan. 5, 1987

[30] Foreign Application Priority Data

Mar. 12, 1986 [DE] Fed. Rep. of Germany ....... 3608210

[51] Int. Cl.$^4$ .................... C07C 29/76; C07C 31/10
[52] U.S. Cl. ..................................... 568/917; 568/922
[58] Field of Search ................................ 568/922, 917

[56] References Cited

U.S. PATENT DOCUMENTS

| 2,628,986 | 2/1953 | Wallace et al. | 568/917 |
| 2,713,075 | 7/1955 | Doeringer et al. | 568/922 |
| 3,433,841 | 3/1969 | Dehn et al. | 568/917 |
| 4,219,685 | 8/1980 | Savini | 568/922 |

*Primary Examiner*—J. E. Evans
*Attorney, Agent, or Firm*—Robert A. Kulason; James J. O'Loughlin; Robert B. Burns

[57] ABSTRACT

A process for deodorizing technical-grade isopropyl alcohol by contacting the alcohol with a strongly acidic cation exchange resin loaded with silver in ionic form is provided.

8 Claims, No Drawings

PROCESS FOR DEODORIZING ISOPROPYL ALCOHOL

FIELD OF THE INVENTION

This invention relates to a process for deodorizing isopropyl alcohol. More particularly, it relates to the deodorizing of isopropyl alcohol which has been produced by the catalytic hydration of propene in the presence of a sulfonated styrene-divinylbenzene resin catalyst.

Isopropyl alcohol is produced by the reaction of propene with sulfuric acid or by direct hydration on a sulfonated cation exchange resin. This isopropyl alcohol contains traces of different compounds which impart to the technical-grade product an unpleasant odor that makes it unsuitable for a variety of uses and, particularly, for use in the cosmetic and pharmaceutical industry.

The contaminants considered responsible for causing the odor in isopropyl alcohol are only partly detectable by gas chromatographic analyses. Their content in the technical-grade alcohol is in the order of parts per billion (ppb). They are comprised of organic sulfur compounds, such as hydrogen sulfide, carbonyl sulfide, and mercaptans. At the present time, expensive treatment procedures have been necessary, such as distillation and adsorption processes, to free the technical-grade alcohol from these substances. Deodorization by active carbon treatment has been performed for many years. However, it is necessary to reactivate the active carbon at regular intervals by expensive steam treatment. Even this treatment has limitations. Only a few active carbon absorbents are suitable. Some produce too many by-products, such as acetone, or cannot be reactivated, or can be reactivated only to a limited extent or are not sufficiently efficient for deodorization.

DISCLOSURE STATEMENT

U.S. Pat. No. 2,857,436 discloses a process for improving the odor of lower technical-grade alcohols by contacting them with a fine silicious iron material having a large surface area. In another embodiment of the process of said patent specification, the lower alcohols are contacted with unglazed porcelain and steel wool in order to improve the odor.

U.S. Pat. No. 2,729,682 discloses a process for improving the odor of isopropyl alcohol by adding during the production $C_4$–$C_6$ mono-olefins to the propylene stream, reacting with sulfuric acid, and hydrolyzing the reaction product while simultaneously reacting at temperatures of up to 300° C. the $C_4$–$C_4$ olefin contained therein together with the contaminants causing the odor to form higher boiling contaminants. The purified isopropyl alcohol is then obtained by extractive distillation with water.

U.S. Pat. No. 4,219,685 disclosed the deodorization of $C_2$ and $C_3$ alcohols at an elevated temperature in the presence of hydrogenation-active metals, particularly nickel and platinum metals, supported on inorganic material.

U.S. Pat. No. 4,340,769 discloses a method for the preparation of lower aliphatic alcohols by the hydration of an olefin over a catalyst. This disclosure is incorporated by reference.

The processes of the prior art are either complicated and expensive, or during the treatment suggested produce additional contaminants, particularly ketones and ethers.

It is the object of this invention to make available a deodorization process that largely takes away the unpleasant odor of the technical-grade product, that is easy to handle and involves low cost, and that for its part does not form objectionable by-products, such as ketones and ethers.

SUMMARY OF THE INVENTION

In accordance with the invention, isopropyl alcohol which is malodorous or contains an objectionable odor for certain uses is deodorized by contacting the isopropyl alcohol with a strongly acidic cation exchange resin catalyst which has been treated with silver in ionic form and which has been neutralized with an alkali metal or an alkaline earth metal hydroxide.

DETAILED DESCRIPTION OF THE INVENTION

It has been discovered that isopropyl alcohol having an objectionable odor for many commercial applications may be efficiently and economically deodorized by contacting the isopropyl alcohol with a strongly acidic ion exchange resin catalyst which has been treated with or impregnated with silver in an ionic form, as with a silver salt and which has been neutralized with an alkaline earth metal hydroxide or an alkali metal hydroxide.

The isopropyl alcohol requiring a purification treatment may contain sulfur compounds in concentrations measured in parts per billion. In general, the malodorous sulfur compounds may be present in a concentration ranging from about 0.1 to 50 parts per billion. More common concentrations of malodorous components is from about 1 to 25 parts per billion.

The catalyst employed in this process is a silver-treated or impregnated, neutralized strongly acidic ion exchange resin catalyst. A preferred synthetic resin catalyst is a sulfonated styrene-divinyl benzene resin catalyst. Specific preferred synthetic resin catalysts are Amberlyst 15 from Rohm & Haas and LEWATIT SPC 118 from Bayer AG.

The cation exchange resin catalyst is treated with or impregnated or coated with silver ions. This may be done by contacting the cation exchange resin with a solution of a silver compound to effect deposition of the silver ions onto the resin catalyst. The silver concentration on the catalyst should range from about 1 to 25 grams (calculated on the metal basis per liter of cation exchange resin). A preferred concentration is from about 4 to 10 grams, with the most preferred concentration being from about 5 to 8 grams per liter of the cation exchange resin. An objective is to completely load the strongly acidic cation exchange resin to largely avoid acidic catalyst spots which are considered to be responsible for undesirable side reactions.

Neutralization of the cation exchange resin is essential in order to provide an effective deodorizing process for isopropyl alcohol. Neutralization may be further effected either before the cation exchange resin is treated with the silver component or subsequent to treatment with and deposition of silver ions on the cation exchange resin. Neutralization is effected by treatment with an alkaline earth metal hydroxide or with an alkali metal hydroxide. Sodium hydroxide is the preferred agent for effecting neutralization.

According to a preferred embodiment of the process of the invention, the cation exchange resin is first completely neutralized by either completely coating the cation exchange with silver ions, or preferably, prior to the loading with silver, practically completely neutralizing the cation exchange resin with alkali- or alkaline earth hydroxide, particularly with sodium hydroxide. It was suprisingly found that pre-neutralized strongly acidic cation exchange resins, for instance in the sodium form, could be directly loaded with silver ions.

Complete neutralization of the cation exchange resin with Ag ions is possible, but not expedient for economical reasons. It is recommended, according to above alternative embodiment, to practically completely load the cation exchange resin first with inexpensive alkali- or alkaline earth cations, and particularly with sodium cations, and to then treat the pre-neutralized resin with silver ions and to exchange thereby sodium for silver ions.

The deodorization according to the invention is performed by passing the alcohol over the fixed-bed deodorizing resin at atmospheric pressure and ambient temperature. Higher pressures can be employed, but are not necessary.

Elevated temperatures are readily possible particularly when the deodorizing resin is present in practically completely neutralized form. The deodorization is generally performed at 0° to 60° C., particularly at 10° to 50° C., and preferably at 20° to 30° C.

Since the deodorization proceeds very rapidly, high loads of the fixed-bed deodorizing resin, for instance from 0.1 to 15 liters of alcohol/liter of cation exchange resin and hour are possible. Preferably 0.4 to 10 liters of alcohol/liter of cation exchange resin and hour can be put through. The used deodorizing resin can be regenerated the metal being recovered, and can be reused.

The process of this invention is suitable for deodorizing both dry isopropyl alcohol and mixtures of the alcohol with water, and particularly azeotropic isopropyl alcohol.

The following examples illustrate the practice of this invention:

EXAMPLE 1
(COMPARISON EXAMPLE)

A commercial, strongly acidic cation exchange resin, Amberlyst TM 15 from Rohm & Haas Company, was loaded with 7.6 grams of silver (calculated as metal) per liter of resin by treatment with aqueous silver nitrate solution and was used in the acidic form for deodorizing isopropyl alcohol.

0.065 liters of isopropyl alcohol per hour were put through during 24 hours at 50° C. from the top to bottom of a column having a length of 28 cm and a diameter 2.6 cm packed with 0.15 liters of the silver-loaded resin. The gaschromatographic analysis of an isopropyl alcohol sample taken after 24 hours of operating time showed the following increase in contaminants, as compared with the alcohol feed being deodorized:

Lower hydrocarbons —40 ppm,
Diisopropyl ether —390 ppm.

The odor evaluation showed that the odorants contained prior to deodorization had largely been removed, but that a new smell of diisopropyl ether was perceptible.

EXAMPLE 2

A commercial, strongly acidic cation exchange resin, Amberlyst TM 15 from Rohm & Haas Company, was first loaded with 7.6 grams of silver (calculated as metal) per liter of resin by treatment with aqueous silver nitrate solution. Thereafter, the yet free strongly acidic groups of the cation exchanger were completely neutralized by the addition of 1 normal sodium hydroxide solution and the resin washed neutral was used for deodorizing isopropyl alcohol. The deodorization conditions corresponded to those employed in Example 1.

The gaschromatographic analysis of an isopropyl alcohol sample taken after 24 hours of operating time did not reveal any change in composition as compared to the alcohol to be deodorized.

The odor evaluation showed that the odorants contained prior to deodorization had largely been removed and that no new additional smell had been produced.

EXAMPLE 3

A commercial, strongly acidic cation exchange resin, LEWATIT TM SPC 118 from Bayer AG, was first loaded with 8 grams of silver (calculated as metal) per liter of resin by treatment with aqueous silver nitrate solution. This catalyst was then completely neutralized by the addition of 1 normal sodium hydroxide solution, and was used thereafter for deodorizing isopropyl alcohol.

422.4 $m^3$ of isopropyl alcohol, i.e., 0.2 $m^3$/hour or 5.7 liters of isopropyl alcohol per liter of resin were put through the catalyst over 88 days at an average temperature of 22° C. in a column having a length of 100 cm and a diameter of 21 cm containing 35 liters of silver-loaded resin. The deodorizing efficiency of the resin was still effective.

Most of the odorants present in the isopropyl alcohol prior to deodorization were steadily removed during the entire treating period. At no time was any deterioration of the isopropyl alcohol quality observed either due to new contaminants or objectionable smells.

EXAMPLE 4

A commercial, strongly acidic cation exchange resin of the type Amberlyst TM 15 from Rohm & Haas Company was coated in its inactive, neutral Na+ form with 6 grams of silver (calculated as metal) per liter of resin by treatment with aqueous silver nitrate solution. This catalyst was then used for deodorizing isopropyl alcohol.

A total of 226,388 $m^3$ of isopropyl alcohol, i.e., an average of about 15 $m^3$ of alcohol per hour or 3 parts by volume of alcohol per part by volume of deodorizing resin were put through the catalyst over 643 days at 20° C. from the top to the bottom of a deodorizing column with a total of 5 $m^3$ of the silver-treated deodorizing resin described. The maximum throughput during this time was 20 $m^3$ per hour.

The deodorization efficiency of the resin was still effective following the above alcohol processing. During the entire period the odor evaluation of the deodorized isopropyl was good. No new smells or contaminants were observed.

The foregoing examples illustrate the surprising effectiveness of the process of the invention for deodorizing isopropyl alcohol.

What is claimed is:

1. A process for deodorizing isopropyl alcohol which has been produced by hydration of propene characterized by containing trace amounts of odor-forming components which comprises contacting said isopropyl alcohol with a strongly acidic cation exchange resin catalyst wherein said catalyst has been treated by the steps comprising
   (a) loading a strongly acidic cation exchange resin being neutralized with an alkali or an alkaline earth metal hydroxide with silver in ionic form, or (b) loading a strongly acidic cation exchange resin with silver in ionic form and subsequently effecting neutralization with an alkali or an alkaline earth metal hydroxide.

2. A process according to claim 1 in which said isopropyl alcohol is contacted with said cation exchange resin catalyst in a fixed-bed reactor.

3. A process according to claim 1 in which said cation exchange resin catalyst contains from about 1 to 25 grams of silver ions calculated as silver metal per liter of said cation exchange resin.

4. A process according to claim 1 in which said cation exchange resin catalyst contains from about 4 to 10 grams of silver ions per liter of said cation exchange resin.

5. A process according to claim 1 in which said deodorization is conducted at a temperature ranging from about 10° to about 50° C.

6. A process according to claim 1 in which said deodorization is conducted at a temperature in the range from about 20° to 30° C.

7. A process according to claim 1 in which said deodorization of isopropyl alcohol is conducted at a rate from about 0.4 to 10 liters of isopropyl alcohol/liter of said cation exchange resin and hour.

8. A process according to claim 1 in which said neutralization is effected with sodium hydroxide.

* * * * *